(12) United States Patent
Oh et al.

(10) Patent No.: US 12,279,931 B2
(45) Date of Patent: Apr. 22, 2025

(54) EXPANDABLE COMPRESSION BANDAGE FOR HEMOSTASIS

(71) Applicant: INDUSTRY-ACADEMIC COOPERATION FOUNDATION, YONSEI UNIVERSITY, Seoul (KR)

(72) Inventors: Young Jun Oh, Seoul (KR); Tae Dong Kweon, Seoul (KR); Yong Beom Lim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1450 days.

(21) Appl. No.: 16/461,037

(22) PCT Filed: Nov. 13, 2017

(86) PCT No.: PCT/KR2017/012799
§ 371 (c)(1),
(2) Date: May 15, 2019

(87) PCT Pub. No.: WO2018/093104
PCT Pub. Date: May 24, 2018

(65) Prior Publication Data
US 2020/0060878 A1    Feb. 27, 2020

(30) Foreign Application Priority Data
Nov. 16, 2016    (KR) .................. 10-2016-0152512

(51) Int. Cl.
A61F 13/0203    (2024.01)
A61F 13/00    (2024.01)

(52) U.S. Cl.
CPC .... A61F 13/0213 (2013.01); A61F 13/00063 (2013.01)

(58) Field of Classification Search
CPC .......... A61F 13/00017; A61F 13/00034; A61F 13/00038; A61F 2013/00106;
(Continued)

(56) References Cited

U.S. PATENT DOCUMENTS 4,224,945 A * 9/1980 Cohen ............... A61F 13/00068
602/53
5,271,940 A * 12/1993 Cleary ............... A61F 13/0259
424/443
(Continued)

FOREIGN PATENT DOCUMENTS

CN    205126336    4/2016
JP    2015-154872    8/2015
(Continued)

*Primary Examiner* — Alireza Nia
*Assistant Examiner* — Andrew Jun-Wai Mok
(74) *Attorney, Agent, or Firm* — LEX IP MEISTER, PLLC

(57) ABSTRACT

The present invention is directed to an expandable compression bandage. The expandable compression bandage includes: an adhesive bandage part; and a pressing part including a solvent storage part and an expandable part. The solvent storage part is configured to be attached to a part of an adhesive surface of the adhesive bandage part and to store a swelling solvent, and the expandable part is configured to be disposed beneath the solvent storage part. The expandable part is swollen and expanded when the swelling solvent stored in the solvent storage part is absorbed thereinto.

20 Claims, 9 Drawing Sheets

(58) Field of Classification Search
CPC .... A61F 2013/0017; A61F 2013/00174; A61F 2013/00314; A61F 2013/00327; A61F 13/0206; A61F 13/0213; A61F 2013/00463; A61F 2013/00468; A61F 2013/00472; A61F 2013/00604; A61F 2013/00609; A61F 2013/00676; A61F 2013/00685; A61F 2013/00689; A61F 13/00068; A61F 2013/00217; A61F 2013/00553; A61F 2013/00557; A61F 2013/00646

See application file for complete search history.

(56) References Cited

U.S. PATENT DOCUMENTS

| | | | | |
|---|---|---|---|---|
| 5,643,315 | A * | 7/1997 | Daneshvar | A61F 13/0203 606/202 |
| 5,762,620 | A * | 6/1998 | Cartmell | A61B 50/30 602/42 |
| 5,823,983 | A * | 10/1998 | Rosofsky | D06L 1/18 602/41 |
| 6,998,510 | B2 * | 2/2006 | Buckman | A61F 13/00063 424/443 |
| 9,474,661 | B2 * | 10/2016 | Fouillet | A61F 13/00051 |
| 2010/0297205 | A1 * | 11/2010 | Wenckens | A61P 31/02 514/23 |

FOREIGN PATENT DOCUMENTS

| | | |
|---|---|---|
| KR | 20-2013-0002825 | 5/2013 |
| KR | 10-1432238 | 8/2014 |

* cited by examiner (a)

(b)

(a)

(b)

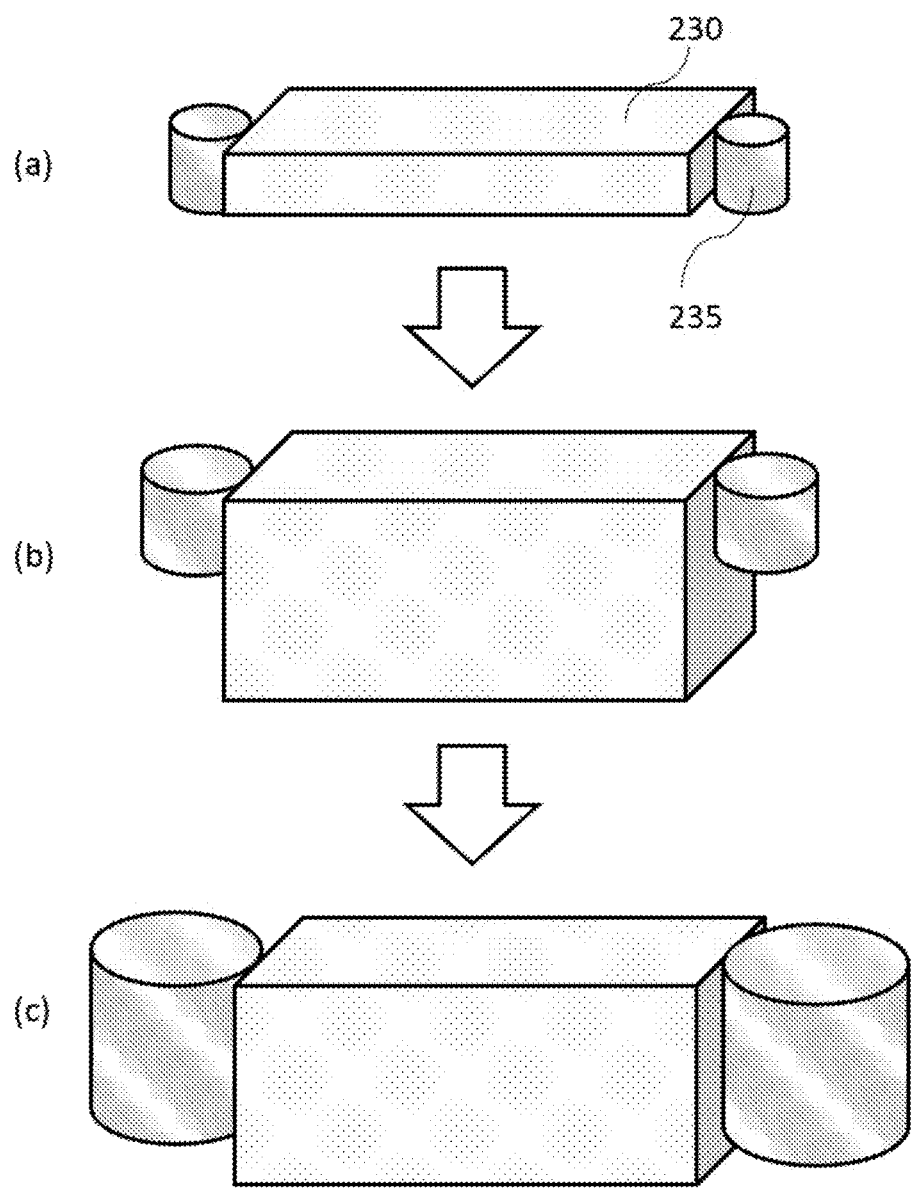

EXPANDABLE COMPRESSION BANDAGE FOR HEMOSTASIS

TECHNICAL FIELD

The present invention relates to a compression bandage for hemostasis, and more specifically to a new expandable compression bandage for hemostasis, which is capable of easily obtaining a hemostatic effect through hemostatic compression by means of a single press.

BACKGROUND ART

Conventionally, when continuous bleeding occurs at a wound or blood collection site, hemostasis is performed by pressing the wound or blood collection site with cotton or attaching a disposable adhesive bandage to the wound or blood collection site. However, the hemostatic effect of this method is weak, and thus there are many difficulties in the performance of hemostasis.

The disposable adhesive bandage merely performs the function of surrounding and being attached to the outer surface of a wound on the skin. Accordingly, an inconvenience arises in that a patient or medical person has to press the outer surface of the adhesive bandage in a direction perpendicular to a bleeding site.

Alternatively, there is used a method of performing emergency treatment by attaching a gauze or cotton pad to a bleeding site and winding an elastic bandage outside the bleeding site. However, the compression bandage and a compression fabric are not sufficiently effective in compression hemostasis for a wound, complete emergency treatment can be performed only when someone else provides a help (someone else helps to tie up), and this method is vulnerable in terms of hygiene. Accordingly, these act as causes of delaying the rapid healing of wounds.

Furthermore, although it depends on the situation of a patient, the time required for hemostasis ranges from 30 minutes to one hour or longer, and thus it is difficult for the patient or a woman to continuously apply hand pressure. Furthermore, the intensity of hand pressure is important, and thus it is uneconomical to spend time in long-term hemostasis.

In order to mitigate the above problems, the invention disclosed in Korean Patent No. 10-1362917 discloses a compression bandage having a hemostatic function, which is capable of performing hemostasis by compressing a wound or blood collection site because a compression nonwoven fabric configured to absorb blood or medicine and then expand is attached to the compression bandage.

FIG. 1 is a schematic diagram of the configuration of a conventional compression bandage having a hemostatic function. As shown in FIG. 1, a compression bandage 1 includes an elastic nonwoven fabric 2 cut to have a predetermined shape and made of a stretchable material. An adhesive surface is formed by applying an adhesive on one surface of the elastic nonwoven fabric 2 which is attached to the skin.

Furthermore, a compressed nonwoven fabric 3 formed by compressing a nonwoven fabric is attached to the adhesive surface of the elastic nonwoven fabric 2 so that the compressed nonwoven fabric 3 comes into close contact with a wound or blood collection site and performs hemostasis through compression during a process of absorbing blood or medicine and expanding.

The compressed nonwoven fabric 3 is formed by rolling a nonwoven fabric in a roll shape and pressing it with a press. When water containing the blood is absorbed into the compressed nonwoven fabric 3, the compressed nonwoven fabric 3 expands due to the property of returning to its original state, and compresses a bleeding site, like in the application of band pressure.

When the compression bandage 1 is attached to a bleeding site on the skin, as described above, blood or medicine is absorbed into the compressed nonwoven fabric 3, and the compressed nonwoven fabric 3 expands in proportion to the quantity of absorbed blood or medicine. Then, the elastic nonwoven fabric 2 is maintained in the state of being attached to the skin, and thus the elastic nonwoven fabric 2 is stretched by the expanded height of the compressed nonwoven fabric 3, thereby performing hemostasis by compressing the bleeding site.

As described above, the conventional hemostatic compression bandage discloses a compression bandage that performs hemostasis through compression attributable to an expanded volume by using the compressed nonwoven fabric and also using the principle in which the nonwoven fabric expands in response to the absorption of blood or medicine when the nonwoven fabric absorbs the blood or medicine. However, in the case of venous blood bleeding having no initial bleeding or a small amount of bleeding, a problem arises in that expansion pressure is weak or insignificant because the amount of blood absorbed into the compressed nonwoven fabric 3 is zero or small and, thus, it is difficult to achieve a hemostatic effect attributable to expansion pressure.

In other words, with regard to hemostasis after the use of an intravenous catheter or after an intravenous injection, a problem arises in that a hemostatic effect is low because compression force applied to a hemostatic site is not high and thus the possibility of edema and infection may be increased.

PRIOR ART DOCUMENTS

Patent Documents (Patent document 1) Korean Patent No. 10-1362917 (issued on Feb. 7, 2014)
(Patent document 2) Korean Patent No. 10-1086038 (issued on Nov. 16, 2011)

DISCLOSURE

Technical Problem

An expandable compression bandage for hemostasis according to the present invention has the following objects:

First, an object of the present invention is to provide an expandable compression bandage for hemostasis, which is capable of easily obtaining a hemostatic effect through hemostatic compression by means of a single press, is capable of selectively and sufficiently increasing hemostatic compression force, and is capable of increasing a hemostatic effect for a low bleeding site, such as a venous blood bleeding site or the like.

Second, an object of the present invention is to provide an expandable compression bandage for hemostasis, which is capable of improving hygiene and also reducing the risk of edema or infection by completely separating blood and a swelling solvent from each other, unlike the conventional bandage, and is capable of monitoring whether or not hemostatic compression is being performed and the hemostatic compression time from the start to the end of hemostatic compression by observing the deformation of an expandable part.

Objects of the present invention are not limited to the above-described objects, and other objects that have not been described above will be clearly understood by those skilled in the art from the following description.

Technical Solution

In order to accomplish the above objects, a first aspect of the present invention provides an expandable compression bandage for hemostasis, the expandable compression bandage including: an adhesive bandage part; and a pressing part including a solvent storage part and an expandable part; wherein the solvent storage part is configured to be attached to a part of an adhesive surface of the adhesive bandage part and to store a swelling solvent, and the expandable part is configured to be disposed beneath the solvent storage part; and wherein the expandable part is swollen and expanded when the swelling solvent stored in the solvent storage part is absorbed thereinto.

In this case, the expandable part may include a hydrogel or alcohol gel as the material thereof, and the swelling solvent may include at least one of water and alcohol.

Furthermore, the expandable compression bandage may further include a medicine storage part configured to store a medicine, including at least one of a disinfectant and a hemostatic agent, beneath the expandable part, the expandable part may expand in two directions toward upward and downward locations or in a single direction toward a downward location, and the expandable compression bandage may further include a blood absorption member disposed beneath the expandable part.

When pressure is applied to the top of the adhesive bandage part, the bottom of the solvent storage part that comes into contact with the expandable part may be at least partially opened such that the swelling solvent is moved to and absorbed into the expandable part. The expandable part may be deformed into at least one shape according to a quantity of the absorbed swelling solvent. The expandable part may enable hemostatic compression time to be monitored based on the shape thereof that varies depending on the quantity of the absorbed swelling solvent.

In addition, the expansion member may be a member in which different materials having different expansion speeds are combined together in a horizontal direction.

A second aspect of the present invention provides an expandable compression bandage for hemostasis, the expandable compression bandage including: an adhesive bandage part; and a pressing part including a solvent storage part, an expandable part and a medicine storage part; wherein the solvent storage part is configured to be disposed beneath the adhesive bandage part and to store a swelling solvent, the expandable part is configured to be disposed beneath the solvent storage part, and the medicine storage part is configured to be disposed on a side surface of the solvent storage part and the expandable part and to store medicines including a disinfectant and a hemostatic agent; wherein the expandable part is swollen and expanded when the swelling solvent stored in the solvent storage part is absorbed thereinto.

The expandable part may include a hydrogel or alcohol gel as the material thereof, the swelling solvent may include at least one of water and alcohol, and the expandable part may expand in two directions toward upward and downward locations or in a single direction toward a downward location.

The expandable compression bandage may further include a blood absorption member disposed beneath the expandable part. When pressure is applied to the top of the adhesive bandage part, the bottom of the solvent storage part that comes into contact with the expandable part may be at least partially opened such that the swelling solvent is moved to and absorbed into the expandable part.

The expandable part may enable hemostatic compression time to be monitored based on the shape thereof that varies depending on the quantity of the absorbed swelling solvent, and the expansion member may be a member in which different materials having different expansion speeds are combined together in a horizontal direction.

Moreover, the pressing part may be detachably attached to a part of the bottom surface of the adhesive bandage part.

Advantageous Effects

The expandable compression bandage for hemostasis according to the present invention has the following effects:

First, the present invention provides the improved expandable compression bandage for hemostasis, which is capable of easily obtaining a hemostatic effect through hemostatic compression by means of a single press via the hemostatic compression part including the solvent storage part and the expandable part that are separated from each other.

Second, the present invention provides the improved expandable compression bandage for hemostasis, which is capable of selectively and sufficiently increasing hemostatic compression force via the stacked structure configured to enable the solvent to be easily absorbed into the expandable part, and is capable of increasing a hemostatic effect for a low bleeding site, such as a venous blood bleeding site or the like, through the increased hemostatic compression force.

Third, the present invention is capable of improving hygiene and reducing the risk of edema or infection by completely separating blood and a swelling solvent from each other, unlike the conventional bandage.

Fourth, the present invention enables the expandable part to be deformed depending on the material and the quantity of the absorbed swelling solvent, thereby providing the considerable advantage of being capable of visually checking whether hemostatic compression is being performed by expansion pressure and the considerable advantage of being capable of monitoring the hemostatic compression time from the start to the end of hemostatic compression in that the deformation varies with time.

Effects of the present invention are not limited to the above-described effects, and other effects that have not been described above will be clearly understood by those skilled in the art from the following description.

DESCRIPTION OF DRAWINGS

FIG. 4 is a schematic side view showing an expandable compression bandage for hemostasis, which includes a pressing part including a solvent storage part 210 configured such that water and alcohol are stored therein and an expandable part configured to use a hydrogel as a material as still another embodiment of the present invention;

FIG. 9 shows views illustrating a structure in which expandable parts of different materials having different expansion speeds are combined together as expandable parts that are applied to an embodiment of the present invention.

Figure 1:
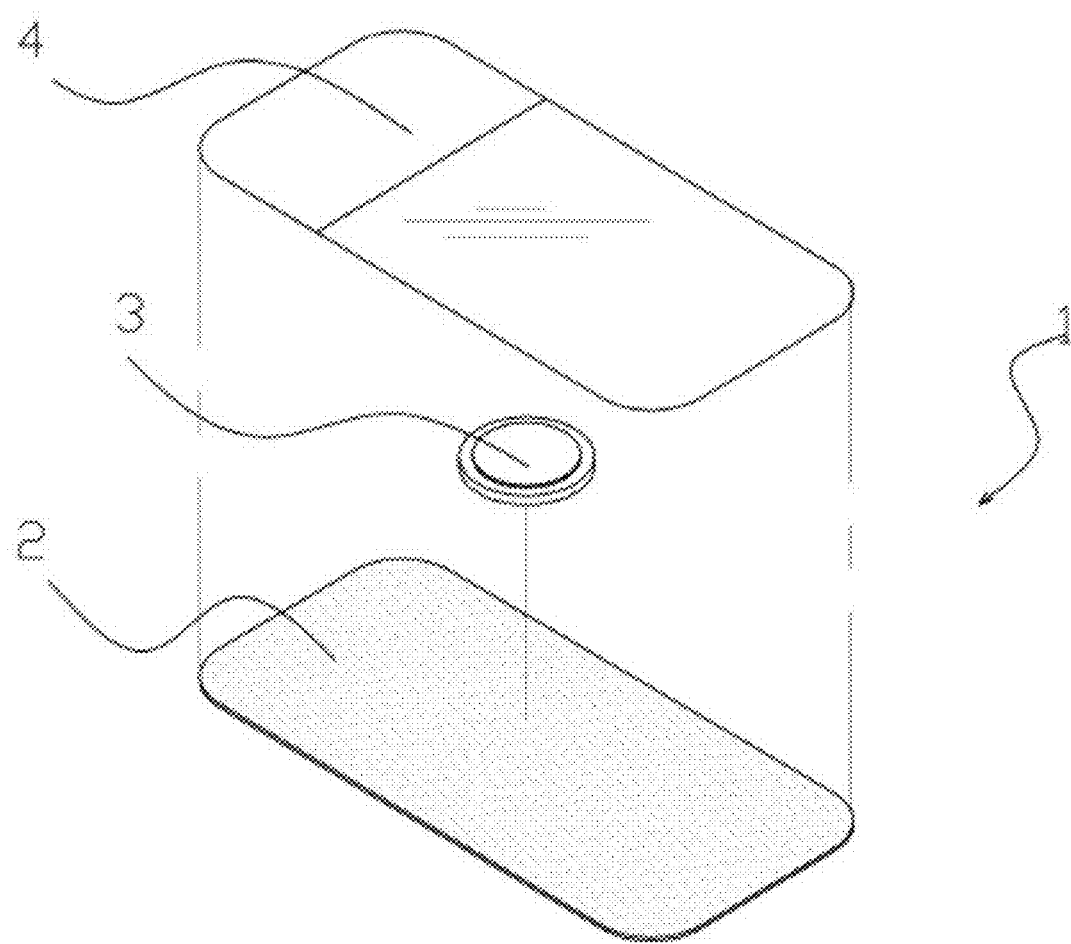
FIG. 1 is a schematic diagram of the configuration of a conventional compression bandage having a hemostatic function.

100: adhesive bandage part 200: pressing part
210: solvent storage part 230: expandable part
250, 270: medicine storage part

BEST MODE

The present invention is directed to an expandable compression bandage for hemostasis, the expandable compression bandage including: an adhesive bandage part; and a pressing part including a solvent storage part configured to be attached to a part of the adhesive surface of the adhesive bandage part and to store a swelling solvent, and an expandable part configured to be disposed beneath the solvent storage part; wherein the expandable part is swollen and expanded when the swelling solvent stored in the solvent storage part is absorbed thereinto.

MODE FOR INVENTION

Additional objects, features and advantages of the present invention will be more clearly understood from the following detailed description and the accompanying drawings.

Prior to the following detailed description of the present invention, it should be noted that the present invention may be subjected to various modifications and may have various embodiments. Accordingly, it should be understood that the present invention is not intended to be limited to specific embodiments described below and illustrated in the accompanying drawings but is intended to encompass all modifications, equivalents and substitutions that fall within the technical spirit and scope of the present invention.

When one component is described as being "connected" or "coupled" to another component, it should be understood that the one component may be directly connected or coupled to the other component or a third component may be present between the two components. In contrast, when one component is described as being "directly connected" or "directly coupled" to another component, it should be understood that a third component is not present between the two components.

The terms used herein are used merely to describe specific embodiments, and are not intended to limit the present invention. A singular expression may include a plural expression unless otherwise defined. In this application, the terms "comprise," "include," "comprising," and "including" and their derivatives are used to designate the presence of one or more features, numbers, steps, operations, components, parts or combinations thereof described in the specification, and should not be understood as excluding the presence or probability of addition of one or more different features, numbers, steps, operations, components, parts or combinations thereof.

Furthermore, the term " . . . part", " . . . unit", or " . . . module" may refer to a unit component that processes at least one function or operation.

In the following description that will be given in conjunction with the accompanying drawings, the same reference numerals will be assigned to the same components throughout the accompanying drawings, and redundant descriptions of the same components will be omitted. In the following description of the present invention, a detailed description of a related well-known technology will be omitted when it is determined that the detailed description may make the gist of the present invention unnecessarily obscure.

Preferred embodiments of the present invention will be described in detail below with reference to the accompanying drawings.

Figure 2:
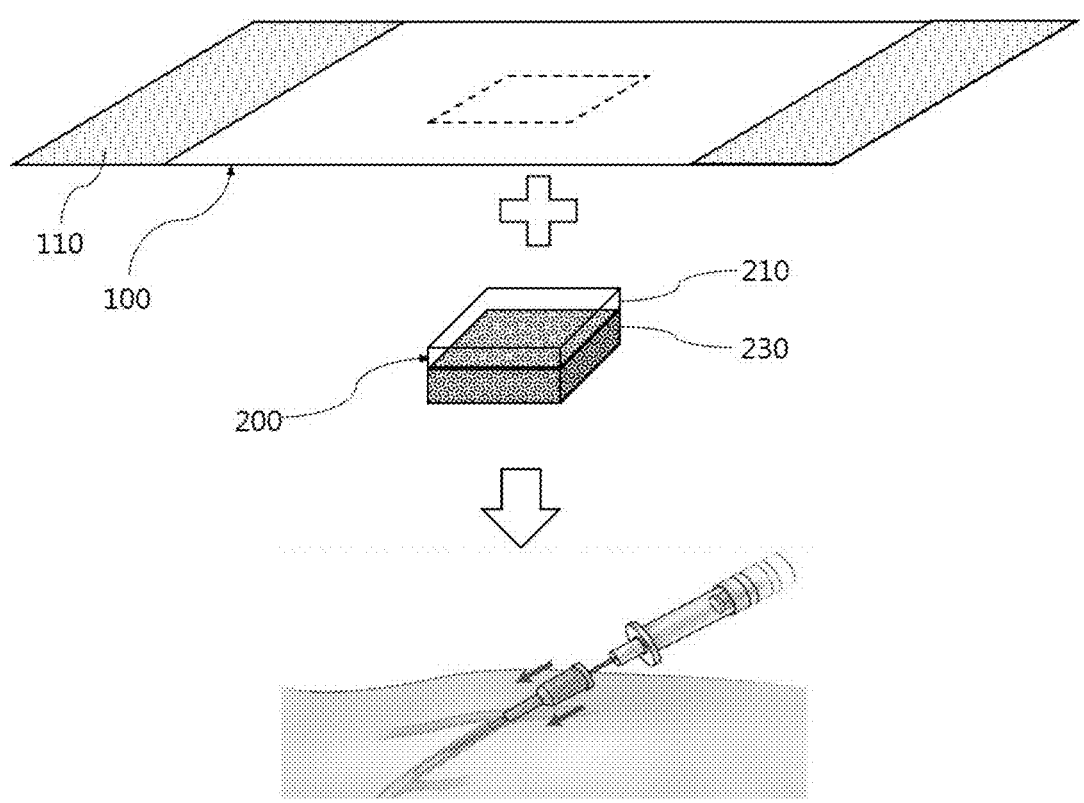
FIG. 2 is an exploded perspective view of an expandable compression bandage for hemostasis according to an embodiment of the present invention.

FIG. 2 is an exploded perspective view of an expandable compression bandage for hemostasis according to one embodiment of the present invention. As shown in FIG. 2, the expandable compression bandage for hemostasis according to the present embodiment of the present invention includes: an adhesive bandage part 100; and a pressing part 200 including a solvent storage part 210 configured to be attached to a part of the adhesive surface of the adhesive bandage part 100 and to store a swelling solvent, and an expandable part 230 configured to be disposed beneath the solvent storage part 210. In this case, the expandable part 230 is swollen and expanded when the swelling solvent stored in the solvent storage part 210 is absorbed thereinto.

In this case, the adhesive bandage part 100 is a bandage having a predetermined shape, which is made of an elastic material, in which an adhesive material is applied to parts of an attachment surface or a circumferential surface so that the adhesive bandage part 100 can be attached to the skin around a blood collection site or the site where a catheter or syringe is inserted, and in which the pressing part 200 for hemostasis is mounted on the center portion of the attachment surface or adhesive surface.

The adhesive bandage part 100 may be formed in various shapes, such as a polygonal shape, a circular shape, an elliptical shape, etc. Any bandage part that is formed in one of the various shapes appropriate for the curve or shape of the skin at a hemostatic site of a patient and that has an easily attachable bandage-type structure is available. The reason for this is that such a surface structure may enhance a hemostatic effect by forming a support surface in order to perform wide surface pressing on a spot-shaped hemostatic site.

As shown in FIG. 2, the pressing part 200 includes the solvent storage part 210 and the expandable part 230 configured to be swollen and expanded when the solvent is absorbed into the expandable part 230. The solvent storage part 210 is a pouch-shaped storage part configured to store the swelling solvent for the expandable part 230, and is a device sealed to prevent the solvent, such as water, alcohol, or the like, from flowing to the outside. The expandable part 230 is made of a material that is swollen or expanded by the swelling solvent when the bottom of the solvent storage part 210 disposed over the expandable part 230 is torn by downward pressure or opened through a hole or the like and thus the solvent flows downward and is absorbed thereinto.

The above-described pressing part 200 in which the solvent storage part 210 is disposed in the upper portion thereof and in which the expandable part 230 is attached to the bottom of the solvent storage part 210 may be configured to be fixedly attached to the center portion or the adhesive bandage part 100, or may be configured to be detachably attached to the center portion or the adhesive bandage part 100. The pressing part 200 that generally comes into contact with blood as a medical device for the hemostasis of blood flowing out of the body of a patient is configured to be detachably attached in that it is limited to single use, and thus the adhesive bandage part 100 may be reused.

In this case, the swelling refers to a phenomenon in which a material absorbs a solvent and is swollen or expanded. The representative materials that generate such a swelling phenomenon include a hydrogel, an alcohol gel, gelatin, etc. As the solvent, any solvent containing moisture, such as water or alcohol, may be used. In one embodiment of the present invention, a material capable of functioning as a solvent to be absorbed into the expandable part 230 and also functioning as a disinfectant to sterilize a hemostatic site is more preferable.

Furthermore, the expandable part 230 applied to one embodiment of the present invention may include the above-described hydrogel, alcohol gel, gelatin, etc. The gelatin is a type of inducible protein obtained by treating collagen, i.e., a natural protein, with hot water, and is used to make ice cream and jellies. This gelatin is completely swollen when it is in water at about 20° C. When the temperature is above 30° C., the gelatin continues to be in the state, and eventually dissolves.

The hydrogel is a gel containing water as a dispersion medium, and is a material formed in such a manner that a hydrosol loses fluidity due to cooling or a hydrophilic polymer having a three-dimensional network structure and a microcrystalline structure is swollen or expanded by containing water. Furthermore, the alcohol gel refers to a material obtained by the gelation of an alcohol component. In addition, any material that can be used as the swelling material or the solvent for the expandable part 230 is available.

According to the above-described embodiment of the present invention, the pressing part 200 is formed by attaching the solvent storage part 210 in which the swelling solvent has been stored and the expandable part 230 to each other, the pressing part 200 is attached to the bottom surface of the adhesive bandage part and brought into contact with the hemostatic site, and then the expandable compression bandage is fastened by attaching attachment surfaces formed on the side surfaces of the adhesive bandage part to the skin. Thereafter, when a user presses the top surface of the adhesive bandage part to which the pressing part 200 has been attached, the lower end surface of the solvent storage part 210 is torn or opened and thus the swelling solvent is absorbed into the expandable part 230, so that the expandable part 230 is naturally swollen and presses a hemostatic site. Accordingly, a new type of expandable compression bandage for hemostasis is proposed.

Figure 3:
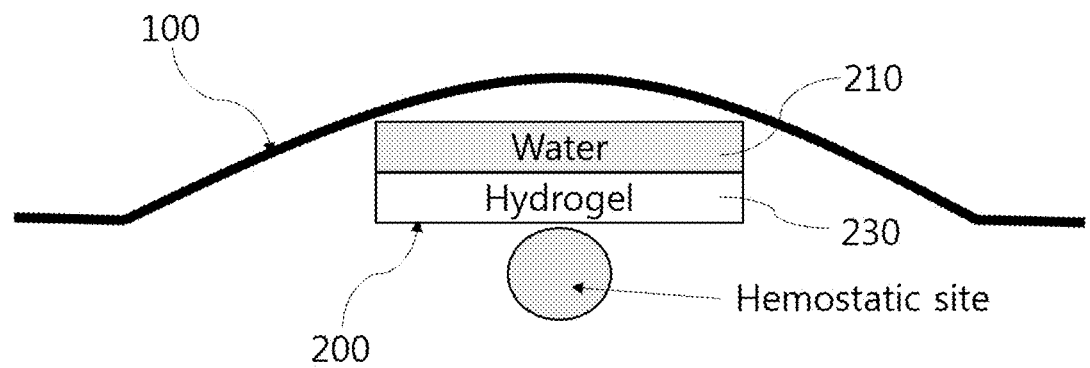
FIGS. 3 to 5 are schematic side views showing the configurations of expandable compression bandages for hemostasis as embodiments of the present invention.
Figure 4:
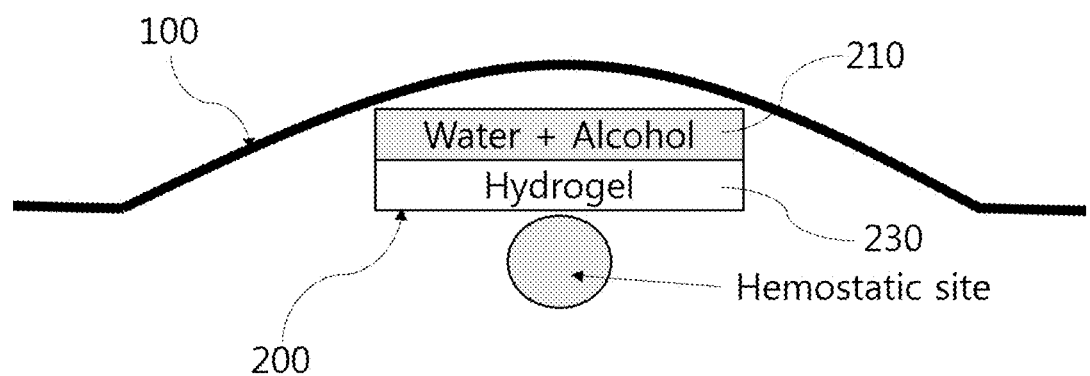
Figure 5:
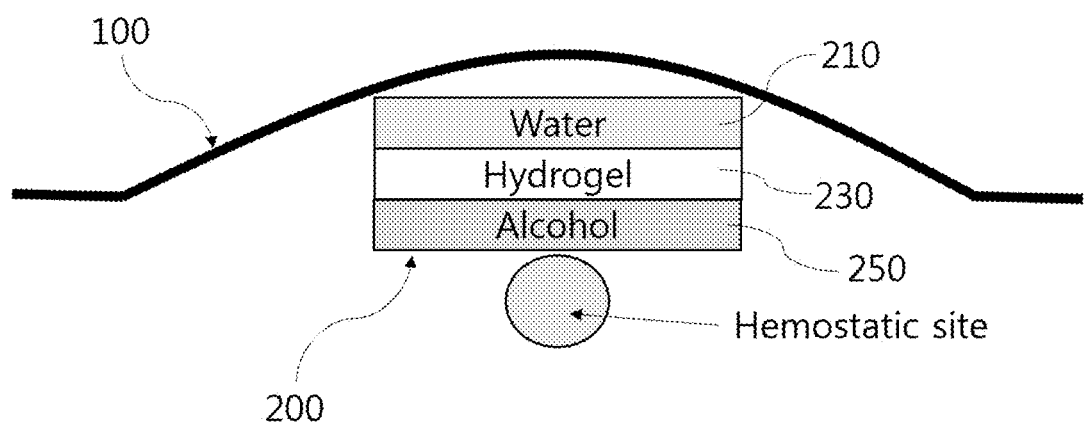

FIGS. 3 to 5 are schematic side views showing the configurations of expandable compression bandages for hemostasis as embodiments of the present invention.

As shown in FIG. 3, the expandable compression bandage for hemostasis according to the embodiment of the present invention includes: a pressing part 200 including a solvent storage part 210 configured to store water as a solvent, and an expandable part 230 configured to be attached to the bottom of a solvent storage part 210 and to use hydrogel, attached to the bottom of the solvent storage part 210, as a material; and a wide adhesive bandage part configured to be attached to the top of the pressing part 200 and to be attached to the skin of a patient or user.

The above-described pressing part 200 is brought into contact with an injection site or hemostatic site of a human body, and the upper adhesive bandage part is attached to the skin around the hemostatic site. Thereafter, when a user presses the top of the adhesive bandage part, the bottom surface of the solvent storage part 210 is pressed and is thus torn or opened to form a hole by pressing force, so that the water stored in the solvent storage part 210 is absorbed into the hydrogel, i.e., the expandable part 230, and starts to be swollen.

As the swelling increases in proportion to the degree of absorption of water, hemostatic compression is naturally performed by the expansion pressure that presses the hemostasis site. As described above, the conventional bandage is inconvenient in that a medical person needs to directly press the top of the bandage by hand and to maintain the state during hemostasis. In contrast, when the expandable compression bandage for hemostasis according to the embodiment of the present invention is employed, a hemostatic effect through hemostatic compression may be easily obtained by means of a single press. Furthermore, it is not necessary to maintain a pressed state until the end of hemostasis from the outside.

Furthermore, the expandable compression bandage for hemostasis according to the embodiment of the present invention has the considerable advantage of increasing a hemostatic effect for a low bleeding site, such as a venous blood bleeding site or the like, because the expandable compression bandage may sufficiently increase hemostatic compressing force via a stacked structure, more specifically a structure capable of easily supplying the solvent of the solvent storage part 210, located over the expandable part 230, to the expandable part 230, unlike the conventional compression bandage for hemostasis that makes use of the expandable part 230 that swells using blood as a solvent.

FIG. 4 shows an expandable compression bandage for hemostasis, which includes a pressing part 200 including a solvent storage part 210 configured such that water and alcohol are stored therein and an expandable part 230 configured to use a hydrogel as a material as still another embodiment of the present invention.

As shown in FIG. 4, a solvent in which water and alcohol are mixed together is stored in the solvent storage part 210. Accordingly, when a user presses the top of the adhesive bandage part, the bottom surface of the solvent storage part 210 is pressed and is thus torn or opened to form a hole by pressing force, so that the water stored in the solvent storage part 210 is absorbed into the hydrogel of the expandable part 230 and starts to be swollen. In this case, the expandable part 230 is swollen in a state in which the hydrogel, the water and the alcohol are mixed together, and compresses a hemostatic site.

As described above, the expandable part 230 having absorbed the solvent in which water and alcohol are mixed together comes into contact with the hemostatic site, and performs both a hemostatic action based on compression and a disinfecting action based on an alcoholic component for the hemostatic site, so that the possibility of edema and infection is lowered, thereby achieving a safe and high hemostatic effect.

FIG. 5 shows an expandable compression bandage for hemostasis, which includes a pressing part 200 including a solvent storage part 210 configured such that water is stored therein, an expandable part 230 configured to use a hydrogel as a material, and a medicine storage part 250 disposed beneath the expandable part 230 and configured such that disinfecting alcohol is stored therein as still another embodiment of the present invention. In this case, a disinfectant and/or a medicine(s), such as a hemostatic agent and/or the like, may be stored in the medicine storage part 250. The medicine refers to a medicine that is used for medicinal purposes, such as a general medicine, a quasi-drug, or the like.

As shown in FIG. 5, in the present embodiment of the present invention, there is employed the pressing part 200 including the solvent storage part 210 configured such that water is stored therein, the expandable part 230 disposed beneath the solvent storage part 210 and made of a hydrogel, and the medicine storage part disposed beneath the expandable part 230 and configured such that disinfecting alcohol is stored therein. Accordingly, when a user presses the top of the adhesive bandage part, the bottom surface of the solvent storage part 210 is pressed and is thus opened by pressing force, so that the water stored in the solvent storage part 210 is absorbed into the hydrogel of the expandable part 230 and starts to be swollen. Thereafter, the medicine storage part 250 is pressed by the expandable part 230 and thus the bottom of the medicine storage part 250 is opened, so that both a disinfection function and hemostatic compression are performed.

As described above, according to the present embodiment of the present invention, the water stored in the solvent storage part 210 is absorbed, and thus the expandable part is swollen. Furthermore, the medicine storage part 250 in which the alcohol is stored is pressed, and thus the alcohol flows out of the medicine storage part 250. Accordingly, a disinfecting action is performed, and also a hemostatic function is performed by compressing a hemostatic site through the expansion of the expandable part.

In this case, the medicine storage part 250 in which alcohol is stored is configured to store and seal a disinfectant, such as alcohol. The medicine storage part 250 may be made of a material that is naturally opened by pressing force caused by the expansion of the expandable part 230 and allows a disinfectant to flow out of the medicine storage part 250 by using a thin, elastic material that is easily torn or opened even by a low pressure.

Furthermore, one or more of a variety of disinfectants, such as hydrogen peroxide, chlorhexidine, a povidone-iodine solution, and a boric acid solution, including alcohol, may be stored in the medicine storage part applied to the embodiment of the present invention, and also a medicine, such as a hemostatic agent, may be stored in the medicine storage part. In other words, both hemostatic compression and a sterilization and disinfection function are performed, thereby reducing the risk of edema or infection.

Figure 6:
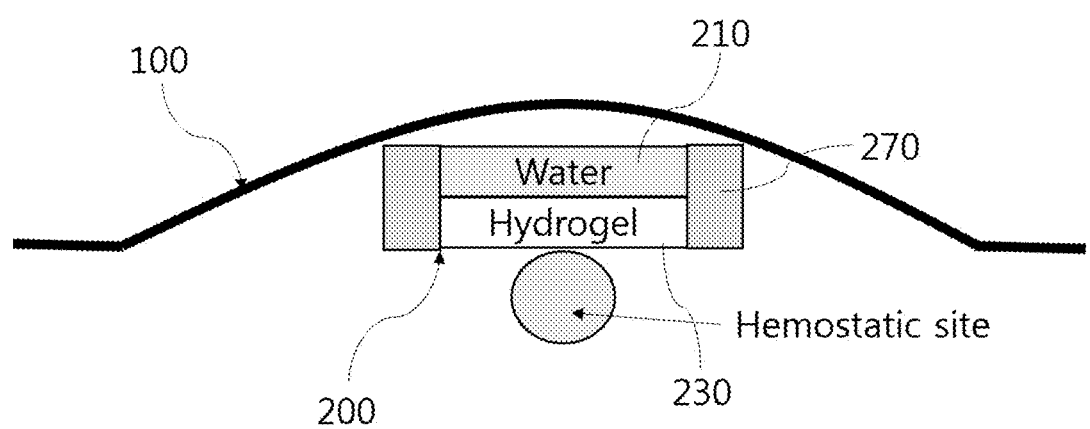
FIG. 6 is a schematic diagram showing the configuration of an expandable compression bandage for hemostasis side surface as still another embodiment of the present invention.

FIG. 6 is a schematic diagram showing the configuration of an expandable compression bandage for hemostasis side surface as still another embodiment of the present invention. As shown in FIG. 6, the expandable compression bandage for hemostasis according to the present embodiment of the present invention includes: an adhesive bandage part 100; and a pressing part 200 including a solvent storage part 210 configured to be disposed beneath the adhesive bandage part 100 and to store a swelling solvent, an expandable part 230 configured to be disposed beneath the solvent storage part 210, and medicine storage parts 270 configured to be disposed on both side surfaces of the solvent storage part 210 and the expandable part 230 and to store medicines, such as a disinfectant, a hemostatic agent, and/or the like. In this case, the expandable part 230 is swollen and expanded when the swelling solvent stored in the solvent storage part 210 is absorbed thereinto.

The present embodiment of the present invention is configured such that the medicine storage parts 270 are attached to and mounted on the side surfaces of the solvent storage part 210 and the expandable part 230, unlike the embodiment of FIG. 4. Water stored in the solvent storage part 210 is absorbed into expandable part 230 by pressing force. At the same time, the medicine storage part 270 is pressed by pressing force and thus the previously stored disinfectant, such as alcohol, flows downward, thereby performing the function of disinfecting a hemostatic site.

Furthermore, in still another embodiment, an expandable compression bandage for hemostasis, including a pressing part 200 in which medicine storage parts 270 are formed on the side surfaces thereof, may include water or alcohol as a solvent stored in a solvent storage part 210, and may store a mixture solvent in which water and alcohol are mixed together.

Furthermore, in addition to the above-described embodiments of FIGS. 3 to 6, a blood absorption member capable of efficiently absorbing blood may be additionally attached to the bottom of the pressing part 200. When the blood absorption member is further included, it completely separates the blood and the swelling solvent from each other, unlike the conventional expandable part 230 configured to absorb blood and then swell, thereby increasing hygiene and also reducing the risk of edema or infection.

Figure 7:
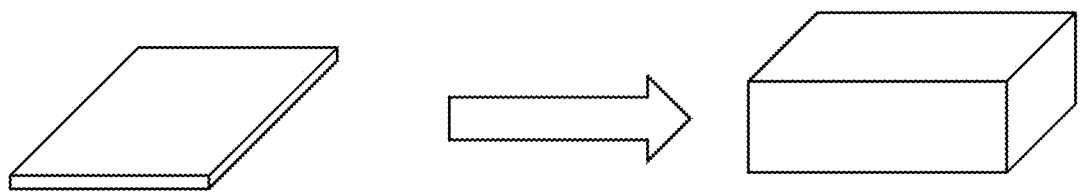
FIGS. 7 and 8 are schematic diagrams of deformation attributable to the expansion of expandable parts used in expandable compression bandages for hemostasis according to embodiments of the present invention.
Figure 7:
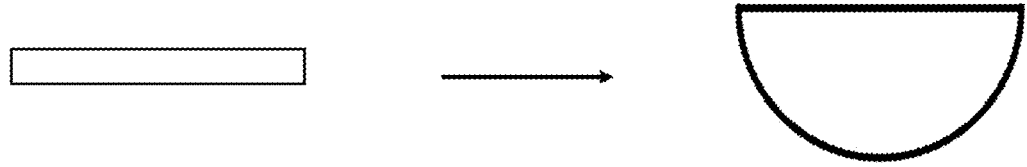
Figure 8:
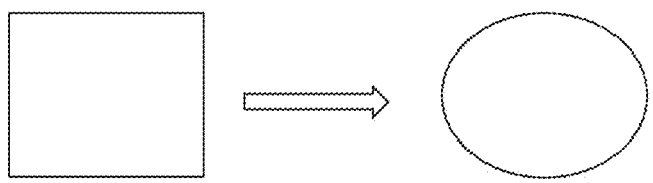
Figure 8:
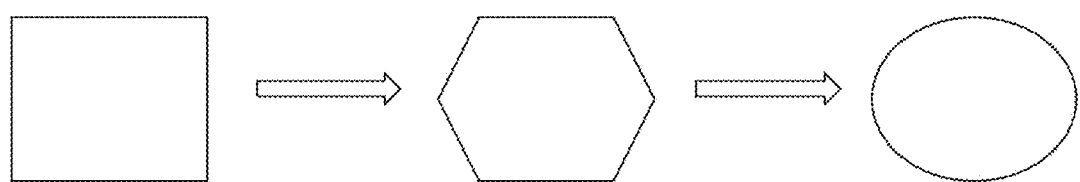

FIGS. 7 and 8 are schematic diagrams of deformation attributable to the expansion of expandable parts 230 used in expandable compression bandages for hemostasis according to embodiments of the present invention.

As shown in FIG. 7, the expandable part 230 may have the property of expanding when it absorbs a swelling solvent, and may use a material the direction of the expansion of which is determined. In other words, the expandable part 230 may use a material that expands in two directions (upward and downward) when absorbing a solvent (see FIG. 7(a)), or may use a material that expands in a semicircular shape when absorbing a solvent (see FIG. 7(b)). Since a compression direction needs to be directed to a hemostatic site, expansion may be performed in a downward direction.

Furthermore, as shown in FIG. 8, as still another embodiment of the present invention, it is preferable that the expandable part 230 uses a material that is deformed into two or more different shapes depending on the quantity of an absorbed swelling solvent, such as water or alcohol. As described above, when the shape of the expandable part 230 itself varies depending on the quantity of the absorbed swelling solvent, the user of the bandage may visually check whether hemostatic compression is desirably performed by a sufficient swelling pressure after pressing. Furthermore, an effect is achieved in that the end time of hemostatic compression may be accurately monitored by taking into account expansion time based on a material and a variation in shape as well as the quantity of the absorbed solvent.

More specifically, the expandable part 230 may use a material that is deformed from a square shape before the absorption of the solvent into a circular shape after the absorption of the solvent at a single step, as shown in FIG. 8(a), or may use a material that is deformed from a square shape before the absorption of the solvent into a hexagonal shape at a first step and is additionally deformed into a circular shape at a second step, as shown in FIG. 8(b). The deformation of the expansion member may vary depending on the material and the quantity of the absorbed swelling solvent. In this case, whether hemostatic compression is desirably performed by an expansion pressure may be visually checked. Furthermore, a considerable advantage arises in that the hemostatic compression time from the start to the end of hemostatic compression may be monitored in that the deformation varies with time.

As described above, a material having a shape memory function is used as the hydrogel used as the expandable parts in the embodiments of the present invention, and thus the deformation of the material is caused by the absorption of the solvent, so that hemostatic compression time may be monitored through the deformation.

In this case, since various researches on hydrogels having a shape memory function have been conducted so far, the customized use of various materials is possible. Technically, it is possible to realize a deformation function by using the property that a molecular arrangement, molecular length, molecular flexibility, etc. inside the hydrogel vary depending on the presence or absence of binding with the solvent.

FIG. 9 shows views illustrating a structure in which expandable parts of different materials having different expansion speeds are combined together as expandable parts that are applied to an embodiment of the present invention.

As shown in FIG. 9, in the present embodiment of the present invention, an expandable part in which different types of materials having different expansion speeds are combined together may be used beneath a solvent storage part. In other words, as shown in FIG. 9(a), there may be used a structure in which expandable parts 235 of a different material having a different expansion speed are disposed on both sides of a single compressive expandable part 230 configured to compress a hemostatic site in a horizontal direction.

Furthermore, as shown in FIG. 9(b), when a solvent is absorbed due to the opening of a solvent storage part, the center compressive expandable part 230 having a fast expansion speed is expanded and presses a hemostatic site.

Then, as shown in FIG. 9(c), after a predetermined time has elapsed, the expandable parts 235 of the different material disposed on both sides of the compressive expandable part 230 and having a slow expansion speed expand, and thus a user may monitor hemostatic compression time.

In other words, a material that completes expansion in accordance with typical hemostasis time may be used as the material of the expandable parts 235 having a slow expansion speed. In this case, a user may check whether the expansion of the expandable parts located on both sides of the compressive expandable part 230 has been completed, and a user or patient may conveniently remove the expandable compression bandage for hemostasis without separately checking the time or requiring the help of a medical person.

The embodiments described herein and the accompanying drawings are intended merely to illustrate part of the technical spirit included in the present invention. Accordingly, the embodiments disclosed herein are not intended to limit the technical spirit of the present invention, but are intended to illustrate the technical spirit. Therefore, it will be apparent that the scope of the technical spirit of the present invention is not limited by the embodiments. All modifications and specific embodiments that can be easily derived by those skilled in the art within the range of the technical spirit included in the present specification and the accompanying drawings should be construed as falling within the range of the rights of the present invention.

The invention claimed is:

1. An expandable compression bandage for hemostasis, the expandable compression bandage comprising:
an adhesive bandage part including an adhesive surface configured to adhered to around a hemostasis site; and
a pressing part including a solvent storage part and an expandable part;
wherein the solvent storage part is attached to a part of the adhesive surface of the adhesive bandage part and stores a swelling solvent, and the solvent storage part is disposed between the adhesive bandage part and the expandable part,
wherein the solvent storage part and the expandable part are configured to be disposed between the hemostasis site and the adhesive bandage part, and
wherein the expandable part is configured to be swollen and expanded to press the hemostasis site when the swelling solvent stored in the solvent storage part is absorbed into the expandable part.

2. The expandable compression bandage of claim 1, wherein the expandable part includes a hydrogel or alcohol gel as a material thereof.

3. The expandable compression bandage of claim 1, wherein the swelling solvent includes at least one of water and alcohol.

4. The expandable compression bandage of claim 1, further comprising a medicine storage part configured to store a medicine, including at least one of a disinfectant or a hemostatic agent, beneath the expandable part.

5. The expandable compression bandage of claim 1, wherein the expandable part expands in two directions toward upward and downward locations or in a single direction toward a downward location.

6. The expandable compression bandage of claim 1, further comprising a blood absorption member disposed beneath the expandable part.

7. The expandable compression bandage of claim 1, wherein when pressure is applied to a top of the adhesive bandage part, a bottom of the solvent storage part that comes into contact with the expandable part is at least partially opened such that the swelling solvent is moved to and absorbed into the expandable part.

8. The expandable compression bandage of claim 1, wherein the expandable part is deformed into at least one shape according to a quantity of the absorbed swelling solvent.

9. The expandable compression bandage of claim 1, wherein the expandable part enables hemostatic compression time to be monitored based on a shape thereof that varies depending on a quantity of the absorbed swelling solvent.

10. The expandable compression bandage of claim 1, wherein the expandable part is a member in which different materials having different expansion speeds are combined together in a horizontal direction.

11. The expandable compression bandage of claim 1, wherein the pressing part is detachably attached to a part of a bottom surface of the adhesive bandage part.

12. An expandable compression bandage for hemostasis, the expandable compression bandage comprising:
an adhesive bandage part including an adhesive surface configured to adhered to around a hemostasis site; and
a pressing part including a solvent storage part, an expandable part and a medicine storage part;
wherein the solvent storage part is disposed beneath the adhesive bandage part and stores a swelling solvent, the solvent storage part is disposed between the adhesive bandage part and the expandable part, and the medicine storage part is disposed on at least one side surface of the solvent storage part and the expandable part and to store medicines including a disinfectant and a hemostatic agent, wherein the solvent storage part and the expandable part are configured to be disposed between the hemostasis site and the adhesive bandage part, and wherein the expandable part is configured to be swollen and expanded to press the hemostasis site when the swelling solvent stored in the solvent storage part is absorbed into the expandable part.

13. The expandable compression bandage of claim 12, wherein the expandable part includes a hydrogel or alcohol gel as a material thereof.

14. The expandable compression bandage of claim 12, wherein the swelling solvent includes at least one of water and alcohol.

15. The expandable compression bandage of claim 12, wherein the expandable part expands in two directions toward upward and downward locations or in a single direction toward a downward location.

16. The expandable compression bandage of claim 12, further comprising a blood absorption member disposed beneath the expandable part.

17. The expandable compression bandage of claim 12, wherein when pressure is applied to a top of the adhesive bandage part, a bottom of the solvent storage part that comes into contact with the expandable part is at least partially opened such that the swelling solvent is moved to and absorbed into the expandable part.

18. The expandable compression bandage of claim 12, wherein the expandable part enables hemostatic compression time to be monitored based on a shape thereof that varies depending on a quantity of the absorbed swelling solvent.

19. The expandable compression bandage of claim 12, wherein the expandable part is a member in which different materials having different expansion speeds are combined together in a horizontal direction.

20. The expandable compression bandage of claim 12, wherein the pressing part is detachably attached to a part of a bottom surface of the adhesive bandage part.

* * * * *